United States Patent [19]

Maier

[11] Patent Number: 4,618,358
[45] Date of Patent: Oct. 21, 1986

[54] HERBICIDAL N-2-(NITRO-5-PHENOXY-PHENYL)-AMINOALKYLPHOSPHONIC ACID AND ESTERS

[75] Inventor: Ludwig Maier, Arlesheim, Switzerland

[73] Assignee: Ciba-Geigy Corporation, Ardsley, N.Y.

[21] Appl. No.: 651,968

[22] Filed: Sep. 19, 1984

Related U.S. Application Data

[62] Division of Ser. No. 484,765, Apr. 14, 1983, abandoned.

[30] Foreign Application Priority Data

Apr. 23, 1982 [CH] Switzerland ............ 2500/82
Nov. 11, 1982 [CH] Switzerland ............ 6585/82

[51] Int. Cl.⁴ ............ A01N 57/06; A01N 57/08; C07F 9/40
[52] U.S. Cl. ............ 71/86; 71/87; 71/94; 558/158; 558/166; 540/24
[58] Field of Search ............ 260/944; 71/86, 87; 558/166, 158

[56] References Cited

U.S. PATENT DOCUMENTS 4,419,124 12/1983 Swithenbaak ............ 260/944
4,456,464 6/1984 Lee et al. ............ 260/944

FOREIGN PATENT DOCUMENTS 0079635 5/1983 European Pat. Off. ............ 944/

Primary Examiner—Anton H. Sutto
Attorney, Agent, or Firm—Edward McC. Roberts; Kevin T. Mansfield

[57] ABSTRACT

The present invention relates to (2-nitro-5-aryloxyphenylamino)alkylphosphonic, -alkylphosphinic and -alkylphosphonous acid derivatives of the general formula I

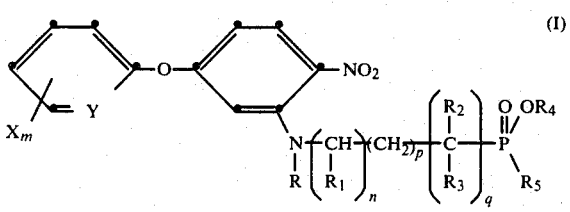

wherein
X is halogen, $CF_3$, $NO_2$, CN, $CONH_2$ or $CSNH_2$,
Y is nitrogen or —CH=,
R is hydrogen, $C_1$–$C_4$alkyl or aralkyl containing 1 to 4 carbon atoms in the alkyl moiety,
$R_1$ is $C_1$–$C_4$alkyl,
$R_2$ is $C_1$–$C_4$alkyl, phenyl or —$PO(OR_6)_2$,
$R_3$ is hydrogen or $C_1$–$C_4$alkyl,
$R_4$ is hydrogen, $C_1$–$C_4$alkyl or a cation,
$R_5$ is hydrogen, $C_1$–$C_4$alkyl, $C_1$–$C_4$haloalkyl, $C_1$–$C_4$alkoxy, hydroxyl or an —O-cation group,
$R_6$ is hydrogen or $C_1$–$C_4$alkyl,
m is a value from 0 to 3,
n is 0 or 1,
p is a value from 0 to 3, and
q is 0 or 1, with the proviso that $R_1$ and $R_3$ taken together may also be an unsubstituted or substituted $C_1$–$C_3$alkylene chain and at least one of the symbols n, p and q is a value different from 0.

These compounds have useful herbicidal properties.

22 Claims, No Drawings

HERBICIDAL N-2-(NITRO-5-PHENOXY-PHENYL)-AMINOALKYLPHOSPHONIC ACID AND ESTERS

This is a division of application Ser. No. 484,765 filed on Apr. 14, 1983 now abandoned.

The present invention relates to (2-nitro-5-aryloxy-phenylamino)alkylphosphonic, -alkylphosphinic and -alkylphosphonous acid derivatives, to the preparation thereof, to herbicidal and growth regulating compositions which contain these compounds, and to the use of said compounds or of compositions containing them for controlling undesired plant growth and for influencing plant growth.

The novel compounds of this invention have the general formula I

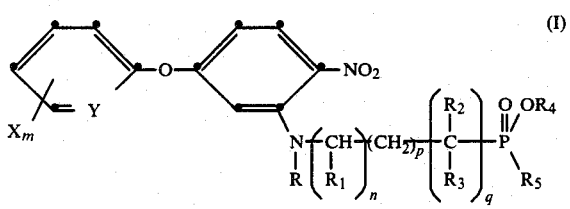

wherein
X is halogen, $CF_3$, $NO_2$, CN, $CONH_2$ or $CSNH_2$,
Y is nitrogen or —CH=,
R is hydrogen, $C_1$–$C_4$alkyl or aralkyl containing 1 to 4 carbon atoms in the alkyl moiety,
$R_1$ is $C_1$–$C_4$alkyl,
$R_2$ is $C_1$–$C_4$alkyl, phenyl or —PO(OR$_6$)$_2$,
$R_3$ is hydrogen or $C_1$–$C_4$alkyl,
$R_4$ is hydrogen, $C_1$–$C_4$alkyl or a cation,
$R_5$ is hydrogen, $C_1$–$C_4$alkyl, $C_1$–$C_4$haloalkyl, $C_1$–$C_4$alkoxy, hydroxyl or an —O—cation group,
$R_6$ is hydrogen or $C_1$–$C_4$alkyl,
m is a value from 0 to 3,
n is 0 or 1,
p is a value from 0 to 3, and
q is 0 or 1,
with the proviso that $R_1$ and $R_3$ taken together may also be an unsubstituted or substituted $C_1$–$C_3$alkylene chain and at least one of the symbols n, p and q is a value different from 0.

In the definition of the formula I, alkyl generally denotes methyl, ethyl, n-propyl, isopropyl, butyl and the isomers thereof. Alkyl will also be understood as meaning the moiety of another radical, e.g. aralkyl, haloalkyl or alkoxy. Halogen denotes in general fluorine, chlorine, bromine or iodine, and is preferably fluorine and, most preferably, chlorine.

Representative examples of aralkyl radicals are phenylalkyl such as benzyl, 2-phenylethyl, 3-phenylpropyl, 1-phenylethyl, 2-phenylpropyl, 1-phenylpropyl, with benzyl being preferred.

Phenyl and arylkyl radicals are unsubstituted or substituted by lower alkyl, halogen, cyano, nitro or lower alkoxy. Unsubstituted phenyl or aralkyl radicals are preferred.

The alkylene chain formed by $R_1$ and $R_3$ contains 1 to 3 carbon atoms and is preferably further substituted by lower alkyl groups. An ethylene or propylene bridge is preferred, with the 2,2-dimethyl-1,3-propylene bridge being most preferred.

Haloalkyl is accordingly in general chloromethyl, dichloromethyl, trichloromethyl, 2-chloroethyl, 1,1,2,2-tetrachloroethyl, perchloroethyl, fluoromethyl, difluoromethyl, trifluoromethyl, 2,2,2-trifluoroethyl, 1,1,2,2-tetrafluoroethyl and perfluoroethyl.

The free acid functions of the phosphinic, phosphonic and phosphonous acids may be in salt form, i.e. their acid protons are replaced by other cations. Such cations are as a rule alkali metal or alkaline earth metal cations; e.g. sodium, potassium, calcium or magnesium cations, or they are substituted ammonium cations such as the cations of dimethylamine, ethylamine, trimethylamine, triethylamine, dishydroxyethylamine, diethylamine, isopropylamine or diisopropylamine; or quaternary ammonium cations such as the trimethylammonium ion, tetraethylammonium ion, trimethylethylammonium ion, triethylmethylammonium ion or diethyldimethylammonium ion.

The direct alkylene chain between the amino group and the phosphonic or phosphinic acid group preferably contains 1 to 3 carbon atoms and may be substituted by further substituents such as lower alkyl radicals, phenyl radicals or phosphonic acid groups or phosphonic acid ester groups.

Preferred compounds of the formula I are those in which
(a) m is 2,
(b) X is trifluoromethyl or chlorine,
(c) R is hydrogen,
(d) the sum of n, p and q together does not exceed 3,
(e) $R_4$ is hydrogen or $C_1$–$C_3$alkyl and
(f) $R_5$ is methyl, ethyl, $C_1$–$C_3$alkoxy or hydroxyl.

Further preferred compounds of the formula I are those in which Y is the —CH= group and m is 2, and both radicals X are chlorine in the 2-position and trifluoromethyl in the 4-position, R is hydrogen, $R_4$ is hydrogen or $C_1$–$C_3$alkyl and $R_5$ is hydrogen, methyl, ethyl, $C_1$–$C_3$alkoxy or hydroxyl, and the sum of n, p and q together does not exceed 3.

Also preferred are the compounds of formula I in which Y is nitrogen, the pyridine ring is etherified in the 2-position, m is 1 and X is trifluoromethyl in the 5-position, R is hydrogen, $R_4$ is hydrogen or $C_1$–$C_4$alkyl and $R_5$ is hydrogen, methyl, ethyl, $C_1$–$C_3$alkoxy or hydroxyl, and the sum of n, p and q together does not exceed 3.

Especially preferred are the compounds of the subformulae

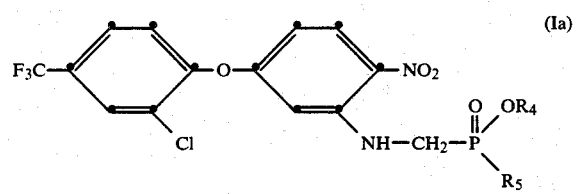

wherein $R_4$ is hydrogen, methyl or ethyl and $R_5$ is methyl or ethyl;

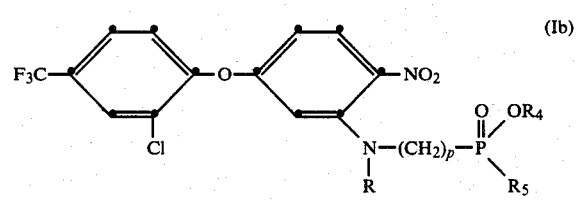

wherein R is hydrogen, methyl or benzyl, R₄ is hydrogen, ethyl or isopropyl, R₅ is hydrogen, hydroxyl, ethoxy or isopropoxy, and p is a value from 1 to 3;

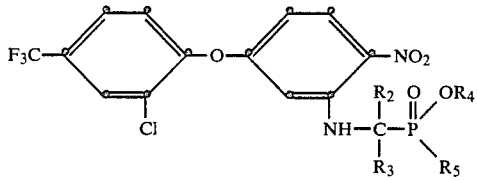

(Ic)

wherein $R_2$ is methyl, $R_3$ is hydrogen or methyl, $R_4$ is hydrogen, ethyl or isopropyl, and $R_5$ is hydroxyl, ethoxy or isopropoxy;

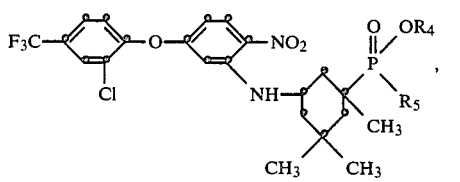

(Id)

wherein $R_4$ is hydrogen, ethyl or isopropyl, and $R_5$ is hydroxyl, ethoxy or isopropoxy; and

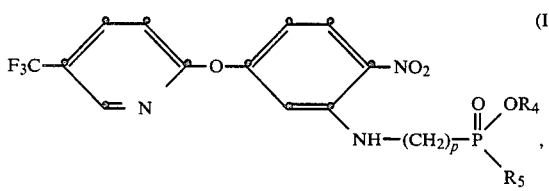

(Ie)

wherein $R_4$ is hydrogen, ethyl or isopropyl, $R_5$ is methyl, hydroxyl, ethoxy or 1-propoxy, and p is a value from 1 to 3.

Preferred individual compounds are:

ethyl N-[2-nitro-5-(2-chloro-4-trifluoromethylphenoxy)phenyl]-P-methylaminomethylphosphinate, diethyl N-[2-nitro-5-(2-chloro-4-trifluoromethylphenoxy)phenyl]-aminomethylphosphonate, dimethyl N-[2-nitro-5-(2-chloro-4-trifluoromethylphenoxy)phenyl]-aminomethylphosphonate, diethyl N-[2-nitro-5-(2-chloro-4-trifluoromethylphenoxy)phenyl]-aminoethylphosphonate, N-[2-nitro-5-(2-chloro-4-trifluoromethylphenoxy)phenyl]-P-methylaminomethylphosphinic acid, ethyl N-[2-nitro-5-(2-chloro-4-trifluoromethylphenoxy)phenyl]-P-ethylaminomethylphosphinate, N-[2-nitro-5-(2-chloro-4-trifluoromethylphenoxy)phenyl]-P-ethylaminomethylphosphinic acid, N-[2-nitro-5-(2-chloro-4-trifluoromethylphenoxy)phenyl]-N-methylaminoethylphosphonous acid, N-[2-nitro-5-(5-trifluoromethyl-2-pyridyloxy)phenyl]-aminopropylphosphonic acid, N-[2-nitro-5-(5-trifluoromethyl-2-pyridyloxy)phenyl]-aminoethylphosphonic acid, and diethyl N-[2-nitro-5-(5-trifluoromethyl-2-pyridyloxy)phenyl]aminoethylphosphonate.

The compounds of formula I are prepared by reacting a dinitrophenylaryl ether of the formula II

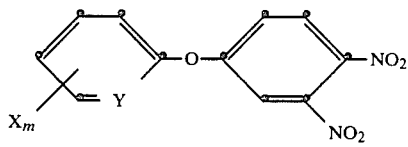

(II)

wherein X, Y and m are as defined for formula I, with an aminoalkylphosphinic acid, aminoalkylphosphonic or aminoalkylphosphonous acid derivative of the formula III

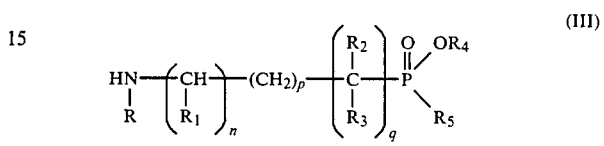

(III)

wherein R, $R_1$, $R_2$, $R_3$, n, p and q are as defined for formula I, and $R_4$ is $C_1$-$C_4$alkyl and $R_5$ is hydrogen, $C_1$-$C_4$alkyl, $C_1$-$C_4$-haloalkyl or $C_1$-$C_4$alkoxy, and, if desired, hydrolysing the reaction product to give the free acid and converting the free acid into a salt by further reaction with a base.

The reaction is conveniently carried out in an aprotic inert organic solvent in the temperature range from 50° to 150° C., preferably from 70° to 120° C.

Suitable solvents are hydrocarbons such as benzene, toluene, xylene, cyclohexane; ethers such as ethylene glycol dimethyl ether, diethylene glycol dimethyl ether, tetrahydrofuran, dioxan; nitriles such as acetonitrile, propionitrile; and dimethyl sulfoxide.

The starting compounds of the formulae II and III are known from European patent specification No. 7471 and from G. M. Kosolapoff and L. Maier, Organic Phosphorus Compounds, Wiley & Sons, New York, Vol. 7 (1976), or they may be obtained by methods corresponding to those indicated in the above publications.

When applied pre- and postemergence to weeds, the compounds of formula I exhibit excellent herbicidal properties. The growth of cultivated plants is influenced only to an insignificant degree unless the compounds of formula I are applied at higher concentrations. The compounds of formula I are therefore particularly suitable for selectively controlling weeds in crops of useful plants such as maize, soybeans, cotton, rice, and cereals such as wheat, barley, rye and oats. Further, the compounds of formula I are particularly suitable for regulating plant growth. In particular, they promote the root growth of cereals and the germination of plant seeds. A number of the compounds of the formula I inhibit the growth of some dicots, e.g. cover crop leguminosae.

Accordingly, the invention also relates to herbicidal and growth regulating compositions which contain a novel compound of the formula I, and to methods of pre- and post-emergence weed control and of growth regulation.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredients) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures of substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepolite or bentonite; and suitable non-sorbent carriers are materials such as calcite or sand. In addition, a great number of preganulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyl laurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$-alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ridgewood, N.J., 1979; Sisley and Wood, "Encyclopedia of Surface Active Agents", Chemical Publishing Co. Inc., New York, 1964.

The pesticidal formulations usually contain 0.1 to 99%, preferably 0.1 to 95%, of a compound of the formula I, 1 to 99% of a solid or liquid adjuvant, and 0 to 25%, preferably 0.1 to 25%, of a surfactant.

Preferred formulations are composed in particular of the following constituents (%=percentage by weight):

| Solutions | | |
|---|---|---|
| active ingredient: | 5 to 95%, | preferably 10 to 80% |
| solvent: | 95 to 5%, | preferably 90 to 0% |
| surfactants: | 1 to 30%, | preferably 2 to 20% |
| Emulsifiable concentrates | | |
| active ingredient: | 10 to 50%, | preferably 10 to 40% |
| surfactant: | 5 to 30%, | preferably 10 to 20% |
| liquid carrier: | 20 to 95%, | preferably 40 to 80% |
| Dusts | | |
| active ingredient: | 0.5 to 10%, | preferably 2 to 8% |
| solid carrier: | 99.5 to 90%, | preferably 98 to 92% |
| Suspension concentrates | | |
| active ingredient: | 5 to 75%, | preferably 10 to 50% |
| water: | 94 to 25%, | preferably 90 to 30% |
| surfactant: | 1 to 30%, | preferably 2 to 25% |
| Wettable powders | | |

| | |
|---|---|
| active ingredient: | 5 to 90%, preferably 10 to 80%, and most preferably, 20 to 60%, |
| surfactant: | 0.5 to 20%, preferably 1 to 15% |
| solid carrier: | 5 to 90%, preferably 30 to 70% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001%. The rates of application are normally 0.1 to 10 kg a.i./ha, preferably 0.25 to 5 kg a.i./ha.

The compositions may also contain further ingredients such as stabilisers, antifoams, viscosity regulators, binders, adhesives, as well as fertilisers or other active compounds, in order to attain special effects.

The invention is illustrated in more detail by the following Examples.

PREPARATORY EXAMPLES

EXAMPLE 1

Diisopropyl N-[2-nitro-5-(2-chloro-4-trifluoromethylphenoxy)-phenyl]-aminomethylphosphonate (compound 1)

A solution of 23.22 g (0.064 mole) of 3',4'-dinitro-2-chloro-4-trifluoromethyl diphenyl ether and 25 g (0.128 mole) of diisopropylaminomethylphosphonate in 120 ml of toluene is refluxed for 16 hours. The dark solution is clarified with activated carbon and the solvent is removed by evaporation, affording 31.38 g (96% of theory) of the title compound in the form of an orange oil which crystallises on cooling with a melting point of 93°–94° C.

Analysis $C_{20}H_{23}ClF_3N_2O_6P$ (510.83): calculated: C 47.03%; H 4.54%; F 11.16%; Cl 6.94%. found: C 47.07%; H 4.82%; F 11.43%; Cl 6.56%.

$^1$H-NMR (CDCl$_3$): δ=1.23 (d; 12H; CH$_3$); 3.43 (dd; $J_{PCH}$=14 Hz; $J_{NHCH}$=5 Hz; 2H; CH$_2$P); 4.7 (m; 2H; OCH); 6.7–8.3 (m; 6H; C$_6$H$_3$); 8–8.5 (br; 1H; NH) ppm.

$^{31}$P-NMR (CDCl$_3$): δ=18.7 ppm.

EXAMPLE 2

N-[2-nitro-5-(2-chloro-4-trifluoromethylphenoxy)-phenyl]-aminomethylphosphonic acid (compound 16)

3.0 (5.9 mmoles) of diisopropyl N-[2-nitro-5-(2-chloro-4-trifluoromethylphenoxy)phenyl]-aminomethylphosphonate are refluxed for 16 hours in 100 ml of 20% hydrochloric acid. The solution is concentrated in vacuo, affording 2.3 g (92% of theory) of the title compound in the form of yellow crystals with a melting point of 148°–150° C.

Analysis $C_{14}H_{11}F_3ClN_2O_6P$ (426.67): calculated: C 39.41%; H 2.60%; N 6.57%. found: C 39.10%; H 2.80%; N 6.70%.

$^1$H-NMR (CDCl$_3$): δ=3.73 (d, J=13 Hz; 2H; CH$_2$P); 4.9 (s; 3H; OH; NH); 5.8–8.0 (m; 6H; C$_6$H$_3$) ppm.

EXAMPLE 3

Ethyl N-[2-nitro-5-(2-chloro-4-trifluoromethylphenoxy)-phenyl]-P-ethylaminomethylphosphinate (compound 10)

A solution of 24.1 g (0.006 mole) of 3',4'-dinitro-2-chloro-4-trifluoromethyl diphenyl ether in 120 ml of toluene is heated to reflux and then 20.0 g (0.132 mole) of ethyl P-ethylaminomethylphosphinate are added dropwise, whereupon nitrose gases evolve. The solution is heated to reflux for another 18 hours and then concentrated. The residue is chromatographed over silica gel with ethyl acetate, affording 16.0 g (51.9% of theory) of the title compound in the form of a yellow oil.

Analysis $C_{18}H_{19}ClF_3N_2O_5P$ (466.78): calculated: C 46.32%; H 4.10%; N 6.00%; P 6.63%. found: C 45.66%; H 4.32%; N 6.29%; P 6.71%.

EXAMPLE 4

Ethyl N-[2-nitro-5-(2-chloro-4-trifluoromethylphenoxy)-phenyl]-P-methylaminomethylphosphinate (compound 8)

A solution of 19.8 g (0.055 mole) of 3',4'-dinitro-2-chloro-4-trifluoromethyl diphenyl ether in 100 ml of toluene is heated to reflux and then 15.0 g (0.1094 mole) of ethyl P-methylaminomethylphosphinate are added dropwise, whereupon nitrose gases evolve. The solution is refluxed for another 30 hours and then concentrated. The residue is chromatographed over silica gel with ethyl acetate, affording 19.07 g (76.6% of theory) of the title compound with a melting point of 118.5°–119.5° C.

Analysis $C_{17}H_{17}ClF_3N_2O_5P$ (452.75): calculated: C 45.10%; H 3.78%; N 6.19%; P 6.84%. found: C 44.94%; H 3.89%; N 6.34%; P 6.79%.

EXAMPLE 5

N-[2-Nitro-5-(2-chloro-4-trifluoromethylphenoxy)-phenyl]-P-methylaminomethylphosphinic acid (compound 9)

8.0 g (0.017 mole) of ethyl N-[2-nitro-5-(2-chloro-4-trifluoromethylphenoxy)phenyl]-P-methylaminomethylphosphinate are refluxed for 14 hours in 50 ml of 20% hydrochloric acid. The precipitated crystalline product is isolated and dried at 80° C. in vacuo, affording 7 g (96.8% of theory) of the title compound with a melting point of 153°–154.5° C.

Analysis $C_{15}H_{13}ClF_3N_2O_5P$ (427.58): calculated: C 42.13%; H 3.16%; N 6.55%; P 7.24%. found: C 42.11%; H 3.23%; N 6.66%; P 7.22%.

EXAMPLE 6

Diethyl N-[2-nitro-5-(2-chloro-4-trifluoromethylphenoxy)-phenyl]-aminoethylphosphonate (compound 4)

A solution of 23.22 g (0.064 mole) of 3',4'-dinitro-2-chloro-4-trifluoromethyl diphenyl ether in 80 ml of toluene is heated to reflux in 80 ml of toluene and then a solution of 24.19 g (0.128 mole) of diethyl aminoethylphosphonate in 40 ml of toluene is added dropwise. The solution is refluxed for 16 hours and then concentrated. The residue is chromatographed over silica gel with a 4:1 mixture of ethyl acetate/hexane, affording 28.35 g (89.2%) of the title compound in the form of a yellow oil.

Analysis $C_{19}H_{21}ClF_3N_2O_6P$ (496.81): calculated: C 45.93%; H 4.26%; N 5.64%; P 6.23%. found: C 44.87%; H 4.20%; N 5.62%; P 5.93%.

EXAMPLE 7

Diethyl N-[2-nitro-5-(2-chloro-4-trifluoromethylphenoxy)-phenyl]-aminomethylphosphonate (compound 12)

A solution of 20 g (0.055 mole) of 3',4'-dinitro-2-chloro-4-trifluoromethyl diphenyl ether in 100 ml of toluene is heated to reflux and then 18.43 g (0.11 mole) of diethyl aminomethylphosphonate are added dropwise. The solution is refluxed for 18 hours and then concentrated. The residue is chromatographed over silica gel with ethyl acetate, affording 14.38 g (58.0%) of the title compound with a melting point of 78°–79° C.

Analysis $C_{18}H_{19}Cl, F_3N_2O_6P$ (482.78): calculated: C 44.78%; H 3.96%; N 5.80%; Cl 7.34%; P 6.40%. found: C 44.71%; H 4.03%; N 5.78%; Cl 7.35%; P 6.39%.

EXAMPLE 8

Monoethyl N-[2-nitro-5-(2-chloro-4-trifluoromethylphenoxy)-phenyl]-N-methylaminoethylphosphonite (compound 24)

With stirring, 15 g (0.0992 mole) of monoethyl N-methylaminoethylphosphonite are added dropwise to a solution of 17.99 g (0.0496 mole) of 3',4'-dinitro-2-chloro-4-trifluoromethyl diphenyl ether in 70 ml of toluene, and the mixture is heated to reflux for 12 hours. After cooling, the mixture is filtered and the filtrate is concentrated. The residue is purified by chromatographed over silica gel with a mixture of hexane/ethyl acetate, concentrated and taken up in chloroform. The chloroform solution is washed with water, dried and concentrated, affording 7.4 g (34.2% of theory) of the title compound in the form of a yellow viscous oil.

Analysis $C_{18}H_{19}ClF_3N_2O_5P$ (466.78): calculated: C 46.32%; H 4.10%; N 6.00%; O 6.63%. found: C 44.8%; H 4.1%; N 6.9%; P 6.5%.

$^1$H-NMR (CDCl$_3$): $\delta$=1.33 (t; 3H; CH$_3$); 2.20 (26; 2H; CH$_2$P); 2.87 (s; 3H; N—CH$_3$); 3.50 (2t; 2H; NCH$_2$); 4.1 (quint.; 2H; OCH$_2$); 6.3–8.0 (m; 6H); 7.3 (d, $J_{PH}$=548 Hz; 1H) ppm.

EXAMPLE 9

N-[2-nitro-5-(2-chloro-4-trifluoromethylphenoxy)-phenyl]-N-methylaminoethylphosphonous acid (compound 25)

A mixture of 3.2 g of monoethyl N-[2-nitro-5-(2-chloro-4-trifluoromethylphenoxy)phenyl]-N-methylaminoethylphosphonite and 10 g of trimethylbromosilane is stirred for 18 hours at 20° C. Excess trimethylbromosilane is removed by evaporation and the residue is then taken up in ethanol and the solution is evaporated, affording as residue a yellow oil which crystallises from ether. Yield: 2.14 g (71.3% of theory) of the title compound with a melting point of 161°–164° C.

EXAMPLE 10

Diethyl N-[2-nitro-5-(5-trifluoromethyl-2-pyridyloxy)phenyl]-aminomethylphosphonate (compound 25)

With stirring, 7.6 g (0.045 mole) of diethyl aminomethylphosphonate are added dropwise to a solution of 15 g (0.045 mole) of (5-trifluoromethyl-2-pyridyloxy)-3,4-dinitrobenzene in 50 ml of toluene, and the mixture is heated for 12 hours to reflux. The mixture is then concentrated and the residue is chromatographed over silica gel with a 1:4 mixture of hexane/ethyl acetate, affording 9.8 g (48.7% of theory) of the title compound with a melting point of 74°–76° C.

Analysis $C_{17}H_{19}S_3N_3O_6P$ (449.30): calculated: C 45.44%; H 4.26%; N 9.35%; P 6.89%. found: C 44.2%; H 4.3%; N 10.1%; P 6.8%.

$^1$H-NMR (CDCl$_3$): $\delta$=1.37 (t; 6H; CH$_3$); 3.7 (2d; 2H; CH$_2$P); 4.2 (quint.; 4H; OCH$_2$); 6.4–8.5 (m; 6H); 8.5 (s, wide; 1H; NH) ppm.

EXAMPLE 11

N-[2-Nitro-5-(5-trifluoromethyl-2-pyridyloxy)phenyl]-aminomethylphosphonic acid (compound 56)

A mixture of 3 g of diethyl N-[2-nitro-5-(5-trifluoromethyl-2-pyridyloxy)phenyl]-aminomethylphosphonate and 5 g of trimethylbromosilane is stirred for 18 hours at 20° C. Excess trimethylbromosilane is removed by evaporation and the residue is then taken up in ethanol and the solution is concentrated, affording 2.51 g (96.9% of theory) of the title compound with a melting point of 94° C. (decompos.).

The compounds listed in the following table are obtained in corresponding manner.

TABLE 1

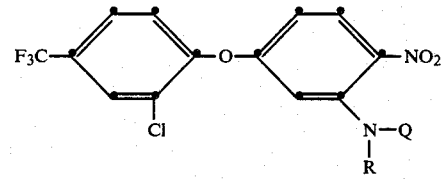

| Compound | R | Q | Physical data |
|---|---|---|---|
| 1 | H | —CH$_2$—PO(O—C$_3$H$_7$—i)$_2$ | m.p. 93–95° C. |
| 2 | H | —(CH$_2$)$_2$—PO(O—C$_3$H$_7$—i)$_2$ | orange oil |
| 3 | H | —CH(CH$_3$)—PO(O—C$_3$H$_7$—i)$_2$ | orange oil |
| 4 | H | —(CH$_2$)$_2$—PO(O—C$_2$H$_5$)$_2$ | yellow oil |
| 5 | CH$_3$ | —CH$_2$—PO(O—C$_3$H$_7$—i)$_2$ | orange oil |
| 6 | H | —(CH$_2$)$_2$—PO(OH)$_2$ | m.p. 226–227.5° C. |
| 7 | H | —CH[PO(O—C$_2$H$_5$)$_2$]$_2$ | yellow oil |
| 8 | H | —CH$_2$—PO(CH$_3$)—OC$_2$H$_5$ | m.p. 118.5–119.5° C. |
| 9 | H | —CH$_2$—PO(CH$_3$)—OH | m.p. 153–154.5° C. |
| 10 | H | —CH$_2$—PO(C$_2$H$_5$)—O—C$_2$H$_5$ | yellow oil |
| 11 | H | —CH$_2$—PO(C$_2$H$_5$)—OH | m.p. 122–124° C. |

TABLE 1-continued

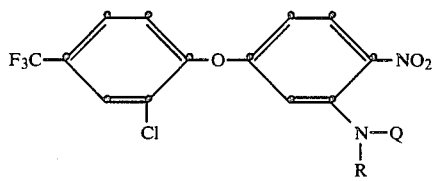

| Compound | R | Q | Physical data |
|---|---|---|---|
| 12 | H | —CH$_2$—PO(O—C$_2$H$_5$)$_2$ | m.p. 78–79.5° C. |
| 13 | CH$_3$ | —CH$_2$—PO(OH)$_2$ | m.p. 126–128° C. |
| 14 | H | —CH[PO(OH)$_2$]$_2$ | m.p. 190° C. (decompos.) |
| 15 | C$_6$H$_5$—CH$_2$— | —CH$_2$—PO(O—C$_3$H$_7$—i)$_2$ | yellow oil |
| 16 | H | —CH$_2$—PO(OH)$_2$ | m.p. 148–150° C. |
| 17 | H | —(CH$_2$)$_3$—PO(O—C$_3$H$_7$—i)$_2$ | orange oil |
| 18 | H | —(CH$_2$)$_3$—PO(OH)$_2$ | m.p. 152–154.5° C. |
| 19 | H | (cyclohexylidene with PO(O—C$_3$H$_7$—i)$_2$, CH$_3$, CH$_3$, CH$_3$) | orange oil |
| 20 | H | —(CH$_2$)$_2$—CH(C$_6$H$_5$)—PO(O—C$_3$H$_7$—i)$_2$ | orange viscous oil |
| 21 | H | —(CH$_2$)$_2$—CH(C$_6$H$_5$)—PO(OH)$_2$ | m.p. 72–76° C. |
| 22 | H | (cyclohexylidene with PO(OH)$_2$, CH$_3$, CH$_3$, CH$_3$) | m.p. 115–118.5° C. |
| 23 | H | —CH$_2$—PO(OCH$_3$)$_2$ | |
| 24 | CH$_3$ | —(CH$_2$)$_2$—PHO—OC$_2$H$_5$ | yellow viscous oil |
| 25 | CH$_3$ | —(CH$_2$)$_2$—PHO—OH | m.p. 161–164° C. |
| 26 | H | —(CH$_2$)$_2$—PHO—OC$_2$H$_5$ | |
| 27 | H | —(CH$_2$)$_2$—PHO—OH | |
| 28 | C$_4$H$_9$—t | —(CH$_2$)$_2$—PHO—OC$_2$H$_5$ | |
| 29 | C$_4$H$_9$—n | —(CH$_2$)$_2$—PHO—OC$_2$H$_5$ | |
| 30 | H | —(CH$_2$)$_2$—PO(CH$_3$)—OH | |
| 31 | H | —(CH$_2$)$_2$—PO(CH$_3$)—OCH$_3$ | |
| 32 | H | —(CH$_2$)$_2$—PO(CH$_3$)—OC$_2$H$_5$ | |

TABLE 2

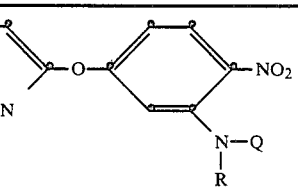

| Compound | R | Q | Physical data |
|---|---|---|---|
| 51 | H | —(CH$_2$)$_3$—PO(O—C$_3$H$_7$—i)$_2$ | m.p. 81–82° C. |
| 52 | H | —CH$_2$—PO(O—C$_2$H$_5$)$_2$ | m.p. 74–76° C. |
| 53 | H | —(CH$_2$)$_2$—PO(O—C$_3$H$_7$—i)$_2$ | m.p. 81–83° C. |
| 54 | H | —(CH$_2$)$_3$—PO(OH)$_2$ | m.p. 134–136° C. |
| 55 | H | —(CH$_2$)$_2$—PO(OH)$_2$ | m.p. 105–106° C. |
| 56 | H | —CH$_2$—PO(OH) | m.p. 94° C. (decompos.) |
| 57 | H | —(CH$_2$)$_2$—PO(O—C$_2$H$_5$)$_2$ | orange viscous oil |
| 58 | H | —CH$_2$—PO(CH$_3$)—OC$_2$H$_5$ | m.p. 88–90° C. |
| 59 | CH$_3$ | —CH$_2$—PO(OC$_2$H$_5$)$_2$ | |
| 60 | CH$_3$ | —CH$_2$—PO(OH)$_2$ | |

FORMULATION EXAMPLES

EXAMPLE 12

Formulation Examples for liquid active ingredients of the formula I (throughout, percentages are by weight)

| (a) Emulsifiable concentrates | (a) | (b) | (c) |
|---|---|---|---|
| compound of formula I | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexane | — | 15% | 20% |
| xylene mixture | 70% | 25% | 20% |

Emulsions of any required concentration can be produced from such concentrates by dilution with water.

| (b) Solutions | (a) | (b) | (c) | (d) |
|---|---|---|---|---|
| compound of formula I | 80% | 10% | 5% | 95% |

-continued

| (b) Solutions | (a) | (b) | (c) | (d) |
|---|---|---|---|---|
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| ligroin (boiling range 160-190°) | — | — | 94% | — |

These solutions are suitable for application in the form of microdrops.

| (c) Granulates | (a) | (b) |
|---|---|---|
| compound of formula I | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| compound of formula I | 2% | 5% |
| highly dispersed silicic acid | 1% | 5% |
| talcum | 97% | — |
| kaolin | — | 90% |

Dusts which are ready for use are obtained by intimately mixing the carriers with the active ingredient.

EXAMPLE 13

Formulation examples for solid active ingredients of the formula I (throughout, percentages are by weight)

| (a) Wettable powders | (a) | (b) |
|---|---|---|
| compound of formula I | 20% | 60% |
| sodium lignosulfonate | 5% | 5% |
| sodium laurylsulfate | 3% | — |
| sodium diisobutylnaphthalene-sulfonate | — | 6% |
| octylphenol polyethylene glycol ether (7-8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| compound of formula I | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50%. |

Emulsions of any required concentration can be obtained from this concentrate by dilution with water.

| (c) Dusts | (a) | (b) |
|---|---|---|
| compound of formula I | 5% | 8% |
| talcum | 95% | — |
| kaolin | — | 92% |

Dusts which are ready for use are obtained by mixing the active ingredient with the carriers, and grinding the mixture in a suitable mill.

| (d) Extruder granulate | |
|---|---|
| compound of formula I | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

| (e) Coated granulate | |
|---|---|
| compound of formula I | 3% |
| polyethylene glycol 200 | 3% |
| kaolin | 94%. |

The finely ground active ingredient is uniformly applied, in a mixer, to the kaolin moistened with polyethylene glycol. Non-dusty coated granulates are obtained in this manner.

| (f) Suspension concentrate | |
|---|---|
| compound of formula I | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

BIOLOGICAL EXAMPLES

EXAMPLE 14

Preemergence herbicidal action

In a greenhouse, plant seeds are sown in flower pots of 12-15 cm diameter. Immediately after sowing, the surface of the soil is treated with an aqueous dispersion or solution of the compounds to be tested. Concentrations of 4 kg a.i./ha are employed. The pots are then kept in the greenhouse at 22°-25° C. and 50-70% relative humidity. The test is evaluated 3 weeks later in accordance with the following rating:

| | |
|---|---|
| 1 | = plants have not germinated or are totally withered |
| 2-3 | = very pronounced action |
| 4-6 | = medium action |
| 7-8 | = insignificant action |
| 9 | = no action (as untreated controls) |

Preemergence Activity

Rate of application: 4 kg a.i./ha

| Compound | Avena | Setaria | Sinapis | Stellaria |
|---|---|---|---|---|
| 1 | 9 | 2 | 1 | 1 |
| 2 | 7 | 4 | 2 | 3 |
| 3 | 7 | 3 | 2 | 3 |
| 4 | 7 | 1 | 1 | 2 |
| 7 | 7 | 6 | 2 | 6 |
| 8 | 4 | 1 | 1 | 1 |
| 9 | 2 | 1 | 1 | 1 |
| 10 | 6 | 1 | 1 | 1 |
| 11 | 7 | 2 | 1 | 4 |

EXAMPLE 15

Test of selectivity in postemergence application

Following the test procedure of Example 14, a large number of plants are treated with different concentrations of test compound. Evaluation is made in accordance with the same scale.

Preemergence activity

| Activity Rate of application in kg a.i./ha | Compound 12 | |
|---|---|---|
| Test plants | 4 | 2 |
| wheat | 8 | 9 |
| maize | 9 | 9 |
| dry rice | 6 | 9 |
| Avena fatua | 2 | 5 |
| Alopecuruc myos. | 2 | 3 |
| Echinochloa c.g. | 1 | 1 |
| Soja | 6 | 9 |
| Rottboellia ex. | 2 | 3 |
| Abutilon | 1 | 1 |
| Xanthium Sp. | 1 | 1 |
| Chenopodium Sp. | 1 | 1 |
| Ipomoea | 1 | 1 |
| Sinapis | 1 | 1 |
| Galium aparine | 1 | 2 |
| Viola tricolor | 1 | 1 |

EXAMPLE 16

Postemergence herbicidal action (contact action)

A number of weeds and cultivated plants, both monocots and dicots, are sprayed postemergence, in the 4- to 6-leaf stage, with an aqueous dispersion of test compound at a rate of application of 4 kg a.i./ha, and then kept at 24°-26° C. and 45-60% relative humidity. The test is evaluated 15 days after treatment using the same scale as in the preemergence test.

Postemergence activity

Rate of application: 4 kg a.i./ha

| Compound | Avena | Setaria | Lolium | Solanum | Sinapis | Stellaria | Phaseolus |
|---|---|---|---|---|---|---|---|
| 1 | 7 | 6 | 7 | 1 | 1 | 5 | 2 |
| 2 | 6 | 4 | 7 | 1 | 1 | 2 | 1 |
| 3 | 6 | 4 | 7 | 1 | 1 | 3 | 3 |
| 4 | 4 | 2 | 4 | 1 | 1 | 1 | 2 |
| 7 | 4 | 5 | 5 | 1 | 1 | 1 | 3 |
| 8 | 1 | 1 | 4 | 1 | 1 | 1 | 4 |
| 9 | 4 | 1 | 5 | 1 | 1 | 1 | 2 |
| 10 | 3 | 1 | 4 | 1 | 1 | 1 | 2 |
| 11 | 4 | 3 | 6 | 1 | 1 | 1 | 2 |
| 12 | 4 | 2 | 6 | 1 | 2 | 2 | 2 |

EXAMPLE 17

Test of selectivity in postemergence application

Following the test procedure of Example 16, a large number of plants are treated with different concentrations of test compound. Evaluation is made in accordance with the same scale as in Example 14.

Postemergence activity

| Activity Rate of application in kg a.i./ha | Compound 8 | |
|---|---|---|
| Test plant | 1 | 0.5 |
| wheat | 6 | 7 |
| maize | 4 | 6 |
| dry rice | 9 | 9 |
| Avena fatua | 2 | 4 |
| Alopecurus myos. | 4 | 4 |
| Echinochloa c.g. | 2 | 3 |
| soybeans | 7 | 8 |
| Abutilon | 1 | 1 |
| Xanthium Sp. | 2 | 2 |
| Chenopodium Sp. | 2 | 2 |
| Sinapis | 2 | 2 |
| Galium aparine | 2 | 3 |
| Viola tricolor | 1 | 1 |

What is claimed is:

1. A (2-nitro-5-aryloxyphenylamino)alkylphosphonic, -alkylphosphonic or -alkylphosphonous acid derivative of the formula

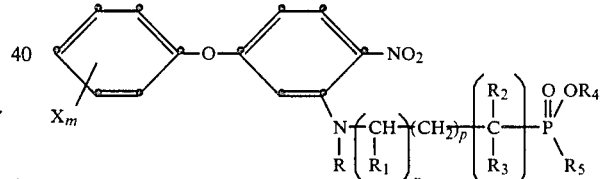

wherein
X is halogen, $CF_3$, $NO_2$, CN, $CONH_2$ or $CSNH_2$,
$R_1$ is $C_1$-$C_4$alkyl,
$R_2$ is $C_1$-$C_4$alkyl, phenyl or —$PO(OR_6)_2$,
$R_3$ is hydrogen or $C_1$-$C_4$alkyl,
$R_4$ is hydrogen, $C_1$-$C_4$alkyl or a cation,
$R_5$ is hydrogen, $C_1$-$C_4$alkyl, $C_1$-$C_4$haloalkyl, $C_1$-$C_4$alkoxy, hydroxyl or an —O—cation group,
$R_6$ is hydrogen or $C_1$-$C_4$alkyl,
m is a value from 0 to 3,
n is 0 or 1,
p is a value from 0 to 3 and
q is 0 or 1,
with the proviso that $R_1$ and $R_3$ taken together may also be an unsubstituted or substituted $C_1$-$C_3$alkylene chain and at least one of the symbols n, p and q is a value different from 0.

2. A method of controlling undesired plant growth or of regulating plant growth, which comprises applying to plants, to the locus thereof or to parts of plants an effective amount of a compound of as claimed in claim 1.

3. A method according to claim 2, which comprises controlling weeds in rice.

4. A compound according to claim 1, wherein m is 2.

5. A compound according to claim 1, wherein X is trifluoromethyl or chlorine.

6. A compound according to claim 1, wherein the sum of n, p and q together does not exceed 3.

7. A compound according to claim 1, wherein $R_4$ is hydrogen or $C_1$–$C_3$alkyl.

8. A compound according to claim 1, wherein $R_5$ is methyl, ethyl, $C_1$–$C_3$alkoxy or hydroxyl.

9. A compound according to claim 1, wherein m is 2, and both radicals X are chlorine in the 2-position and trifluoromethyl in the 4-position, $R_4$ is hydrogen or $C_1$–$C_3$alkyl and $R_5$ is hydrogen; methyl, ethyl, $C_1$–$C_3$alkoxy or hydroxyl, and the sum of n, p and q together does not exceed 3.

10. A compound according to claim 1 of the formula

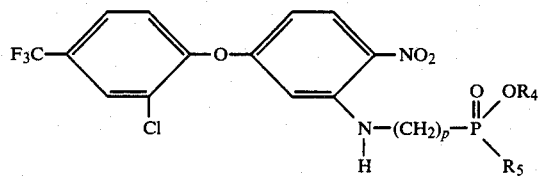

wherein $R_4$ is hydrogen, ethyl or isopropyl, $R_5$ is hydrogen, hydroxyl, ethoxy or isopropoxy, and p is a value from 1 to 3.

11. Ethyl N-[2-nitro-5-(2-chloro-4-trifluoromethylphenoxy)phenyl]-P-ethylaminomethylphosphinate according to claim 11.

12. Ethyl N-[2-nitro-5-(2-chloro-4-trifluoromethylphenoxy)-phenyl]-P-methylaminomethylphosphinate, according to claim 11.

13. Diethyl N-[2-nitro-5-(2-chloro-4-trifluoromethylphenoxy)-phenyl]-aminomethylphosphonate, according to claim 11.

14. Dimethyl N-[2-nitro-5-(2-chloro-4-trifluoromethylphenoxy)-phenyl]-aminomethylphosphonate, according to claim 11.

15. Diethyl N-[2-nitro-5-(2-chloro-4-trifluoromethylphenoxy-phenyl]-aminoethylphosphonate, according to claim 11.

16. N-[2-nitro-5-(2-chloro-4-trifluoromethylphenoxy)phenyl]-P-methylaminomethylphosphinic acid, according to claim 1.

17. N-[2-nitro-5-(2-chloro-4-trifluoromethylphenoxy)phenyl]-P-ethylaminomethylphosphinic acid, according to claim 1.

18. N-[2-nitro-5-(2-chloro-4-trifluoromethylphenoxy)-phenyl]-N-methylaminoethylphosphonous acid, 19. Ethyl N-[2-nitro-5-(2-chloro-4-trifluoromethylphenoxy)-phenyl]-N-methylaminoethylphosphonous acid halfester.

20. A compound according to claim 1 of the formula

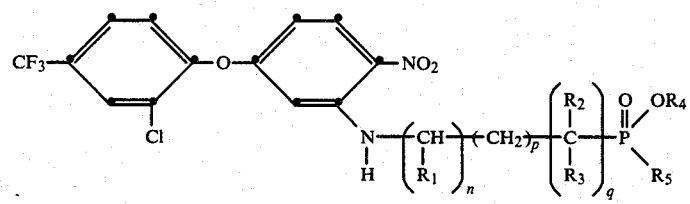

wherein
the sum of n, p and q is 1, 2 or 3,
$R_4$ is hydrogen or $C_1$–$C_3$-alkyl, and
$R_5$ is hydrogen, methyl, $C_1$–$C_3$-alkoxy or hydroxy.

21. A compound according to claim 21 of the formula

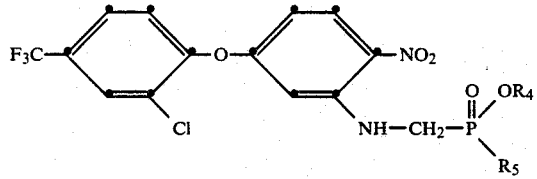

wherein $R_4$ is hydrogen, methyl or ethyl, and $R_5$ is methyl or ethyl.

22. A herbicidal and plant-growth regulating composition which contains, as active component, an effective amount of at least one compound according to claim 1 and a carrier.

* * * * *